United States Patent [19]

Andrews et al.

[11] Patent Number: 5,300,491
[45] Date of Patent: Apr. 5, 1994

[54] TREATMENT OF PROTOZOAL INFECTION

[75] Inventors: Barry J. Andrews, Oslo; Bjarne Bjorvatn, Paradis; Steinar Pedersen, Asker; Jörgen R. Rönnevig, Oslo, all of Norway; Alexander Yule, Harrow, England

[73] Assignee: Apothekernes Laboratorium A.S., Oslo, Norway

[21] Appl. No.: 967,471

[22] Filed: Oct. 23, 1992

Related U.S. Application Data

[63] Continuation-in-part of Ser. No. 785,666, Oct. 31, 1991, abandoned.

[51] Int. Cl.$^5$ .............................................. A61K 37/00
[52] U.S. Cl. ........................................ 514/10; 514/11
[58] Field of Search .................... 514/6, 8, 9, 10, 11

[56] References Cited

U.S. PATENT DOCUMENTS

| | | | |
|---|---|---|---|
| 2,594,374 | 6/1950 | Welch | 424/114 |
| 2,676,134 | 9/1955 | Felsenfeld | 424/114 |
| 2,803,584 | 8/1957 | Hodge et al. | 514/6 |
| 2,903,357 | 9/1959 | Zorn | 514/9 |
| 2,985,533 | 5/1961 | Zorn | 514/9 |
| 3,021,217 | 2/1962 | Zorn | 514/9 |
| 4,693,992 | 9/1987 | Young | 514/11 |
| 5,061,689 | 10/1991 | Alvarez | 514/10 |

OTHER PUBLICATIONS

Adler et al. *J. Bact.* 83, 1315–1317 (1962).
Kadison et al., *The Journal of Pediatrics* 38, pp. 576–589 (1951).
Gillin et al., *Journal of Antimicrobial Chemotherapy* 8, 305–316 (1981).
Sharma et al., *Archives of Opthalmology* 108, 5, p. 625 (May 1990).
Lindquist et al., *Archives of Opthalmology* 106, 1, 73–77 (Jan. 1988).
Most et al., *The American Journal of Tropical Medicine* 30, 493–497 (1950).

*Primary Examiner*—Frederick E. Waddell
*Assistant Examiner*—Kevin F. Weddington
*Attorney, Agent, or Firm*—Seidel, Gonda, Lavorgna & Monaco

[57] ABSTRACT

Protozoal infection of human beings or animals is treated with a divalent metal salt of bacitracin. Some infectious agents sensitive to such treatment include human pathogens such as *Entamoeba histolytica, Trichomonas vaginilis, Giardia lamblia, Cryptosporidium parvum*, and animal pathogens such as *Tritrichomonas foetus* and *Tritrichomonas gallinae*.

18 Claims, No Drawings

TREATMENT OF PROTOZOAL INFECTION

CROSS-REFERENCE TO RELATED APPLICATION

This is a continuation-in-part of co-pending application Ser. No. 785,666, filed Oct. 31, 1991; now abandoned.

FIELD OF THE INVENTION

The invention relates to the treatment of infection by any parasitic or free-living protozoan With divalent metal salts of bacitracin.

BACKGROUND OF THE INVENTION

Protozoa are unicellular eucaryotic microorganisms that lack cell walls. They are generally colorless and motile. Protozoa are distinguished from bacteria by their usually greater size and eucaryotic nature, from algae by their lack of chlorophyll, from yeast and other fungi by their motility and absence of a cell wall, and from the slime molds by their lack of fruiting body formation.

Protozoa usually obtain food by ingesting other organisms or organic particles. Protozoa are found in a variety of freshwater and marine habitats. A large number are parasitic in other animals, including humans. Some protozoa are found growing in soil or in aerial habitats, such as on the surface of trees.

As is appropriate for organisms that "catch" their own food, most protozoa are motile. Their mechanisms of motility are key characteristics used to divide them into major taxonomic groups. Protozoa that move by amoeboid motion are called Sarcodina (common name: amoebas); those using flagella, the Mastigophora (flagellates); and those using cilia, the Ciliophora (ciliates). The Sporozoa, a fourth group, are generally nonmotile and are all parasitic for higher animals.

Typical representatives of the Mastigophora group are Trypanosoma (causing African sleeping sickness), Gtardia, Leishmania, Trichomonas and Tritrichomonas. Members of this protozoal group are motile by the action of flagella.

Among the sarcodines are organisms such as Amoeba and Entamoeba which are always naked in the vegetative phase. *Entamoeba histolytica* is a good example of these parasitic forms.

Ciliates are defined as those protozoa that, in some stage of their life cycle, possess cilia. Typical representatives are *Balantidium* and *Parameclum*. *Balantidium coli* is primarily a parasite of domestic animals, but occasionally it infects the intestinal tract of humans, producing intestinal symptoms similar to those caused by *Entamoeba histolytica*.

The Sporozoa comprise a large group of protozoa, all of which are obligate parasites. Typical sporozoans are *Plasmodium* (causing malaria), *Toxoplasma* and *Cryptosporidium*.

Habitats of endoparasites vary. some are intracellular, such as malarial parasites in vertebrates. Other parasites, such as, *Entamoeba histolytica* invade tissues but not individual cells. Most trypanosomes live in the blood of vertebrate hosts. Many other parasites live in the lumen of the digestive tract or sometimes in coelomic cavities of invertebrates, as do certain gregarines.

Free-living and parasitic protozoans are the cause of many diseases and infections in humans and animals. For example, the protozoan parasite, *Entamoeba histolytica*, is recognized as having infected almost 480 million people. There is no known animal host for the parasite. While the major part of *E. histolytica* infections are of a non-pathogenic nature, over 36 million cases result in clinical disease.

The major proportion of clinical cases of *E. histolytica* infection are present in the form of amoebic dysentery. The amoeba form ulcers in the large intestine. This causes diarrhoea and bleeding into the lumen.

Clinical manifestations of *E. histolytica* infection are mostly restricted to the large bowel. However, if untreated, some of these infections can result in perforation of the large intestine and, under extreme conditions, death from peritonitis.

In other cases of *E. histolytica* infections, extra-intestinal invasion of the parasite may occur. The parasite passes, via the blood or lymphatic system, to abdominal and other organs to produce amoebic abscesses. Under extreme conditions, these infections can also result in severe disease or death.

Metronidazole has been the drug of choice for the treatment of *E. histolytica* since the first report on efficacy was published in 1966 (Powel et al., *Lancet* 2, 1329-31 (1966)). The acute diarrhoea and the liver abscesses associated with *E. histolytica* infection respond well to metronidazole. However, metronidazole has been found to be less effective in asymptomatic cases (Spillman et al., *Am. J. Troy. Med. Hvg.* 25, 549-51 (1976)).

Failure of treatment of *E. histolvtica* infections with metronidazole has been reported with international flight personnel in individual patients (Weber et al., *Trans. RQV. Soc. Troy. Med. Hvg.* 84, 803-5 (1990)). A randomized study of fifty South African patients with amoebiasis revealed a treatment failure with persistent disease in 55% following standard metronidazole therapy of 2.4 g daily for 5 days (Jackson et al., *Symposium on Amoebiasis,* New Delhi, India (1990)).

Although metronidazole is effective in treating *E. histolytica* infections, it has several undesirable side effects. For example, it cannot be administered to pregnant women who are in their first trimester. Moreover, the utility of metronidazole is seriously compromised by its interference with alcohol metabolism. The drug is mutagenic in the Ame's test (Vogd et al., *Mutat. Res.* 26, 483-90 (1974)). Because of its toxic side effects, metronidazole has been covalently linked to silica beads to abolish drug absorption in the treatment of intestinal amoebiasis. Although short term use of metronidazole has been relatively safe, toxic effects of testicular atrophy, ataxia and polyneuropathy has been observed in rats. Metallic taste, headache and peripheral neuropathy are also observed.

Due to the problems associated with the use of metronidazole, there is a need for an alternative method of treating infections by protozoan.

The antibiotic bacitracin has shown a limited capacity to kill both pathogenic and non-pathogenic forms of intestinal amoebic infections (Most et al., *Am. J. Troy. Med.* 30, 491-497 (1950)). For example, in 51 patients, a parasitological cure was obtained in 66% of cases following treatment for 10-20 days with dose ranges of 40,000 to 160,000 units. Extension of therapy beyond 10 days, or an increase in dose to about 80,000 units, did not significantly enhance the probability of cure beyond 66%. The marginal effectiveness of bacitracin in treating amoebiasis has not led to further use of this drug in the treatment of E. histolytica amoebiasis.

Another common disease caused by protozoans is bovine trichomoniasis. Bovine trichomoniasis is a sexually transmitted disease caused by the flagellate protozoan *Tritrichomonas foetus*. Infection by *T. foetus* results in substantial economic losses throughout most of the cattle-rearing areas of the world where natural breeding is relied upon.

*T. foetus* infection is recognized as a significant cause of bovine infertility. This infection touches upon each component of the producer's net income. Specifically, it reduces both, the total number of calves produced and their suckling-growing period. Moreover, *T. foetus* infection results in calves being produced later in the season, thus giving a lighter calf crop which is less uniform in age and weight. Under these circumstances, the calf crop would be unlikely to realize its full market value. In addition, increased feed, treatment, culling and stock replacement costs are incurred. All tolled, it is estimated that, in 1992, *T. foetus* infections will cost the U.S. beef industry approximately 500 million U.S. dollars.

Transmission of *T. foetus* is almost exclusively by coitus. Infection of this type is confined to the reproductive tract with the preferred sites of infection in the bull being the prbputial cavity and the urethral orifice. The prevalence of *T. foetus* infection in bulls generally increases with age and is attributed to the deepening of crypts in the preputial epithelium of older bulls.

Various topical treatments have been proposed for the treatment of *T. foetus* infection in bulls. Examples of such treatments include the implementation of acriflavine salves, chlorohexidine and metronidazole. For the most part, these methods of treatments have proven to be only marginally effective.

The therapeutic value of several 5-nitroimidazole compounds has been established in the treatment of *T. foetus* infection. While multiple oral doses of dimetridazole have been documented as being moderately effective, they can result in undesired side effects such as rumen stasis and anorexia. A single intravenous administration of dimetridazole has also been documented as being moderately effective. However, this too can cause undesired side effects such as respiratory difficulty, ataxia and lung collapse.

Although treatment of *T. foetus* infection with 5-nitroimidazole compounds may be moderately effective, it is prohibitively expensive. For example, in 1991, the cost of each oral administration was approximately $100.00 (U.S.) per bull; and, the cost of an intramuscular administration was approximately $50.00 (U.S.) per bull. Moreover, the use of 5-nitroimidazole compounds is not approved by the U.S. Food & Drug Administration. One such compound, ipronidazole has been declared a suspect carcinogen.

As can be seen, the control of bovine trichomoniagis poses an enormous problem, even in the comparatively well-managed beef herds of the United States. This problem has grown to such proportions that a joint task force comprising the Californian Cattlemen's Association, the U. S. Animal Health Association and the Livestock Disease Research Laboratory has declared bovine trichomoniasis research as having the highest priority.

Other examples of free-living and parasitic protozoans which infect humans or animals include, without limitation, *Trichomonas vaginalis, Tritrichomonas gallinae, Giardia lamblia, Cryptosporidium parvum, Cryptosporidium sp., and Plasmodium Sp.* These and other protozoan organisms are known to cause the following diseases: trichomoniasis, giardiasis, cryptosporidiosis, malaria, babesiosis, theileriosis, toxoplasmosis and leishmaniasis, in addition to all other intestinal and systemic protozoan infections.

An effective treatment against free-living and parasitic protozoan infections of humans and animals is needed. Such a treatment must not only lack the harmful side effects of metronidazole, but also, must be more effective than bacitracin.

SUMMARY OF THE INVENTION

A method is provided for the treatment of infection of humans or animals by free-living or parasitic protozoan. This method comprises administering, to such an infected human or animal, an effective amount of a divalent metal salt of bacitracin.

The invention also relates to the use of such bacitracin salts for the manufacture of medicaments useful in the treatment of infections of humans or animals by free-living or parasitic protozoans.

DETAILED DESCRIPTION OF THE INVENTION

We have found that, when divalent metal salts of bacitracin are administered to humans and animals infected by free-living and/or parasitic protozoan, in most instances, the bacitracin salts are more effective than uncomplexed bacitracin.

As used herein, the phrases "treat", "treatment", "treating" and "need of such treatment" refer to both, the prophylaxis of an asymptomatic human or animal exposed to possible protozoan infection, as well as the therapeutic treatment of an infected human or animal.

As used herein, the term "bacitracin" refers to all of the various forms of bacitracin, and any mixture thereof. This includes, without limitation, bacitracin A, $B_1$, $B_2$, $B_3$, $C_1$, $C_2$, and $C_3$.

As used herein, the terms "divalent metal salts of bacitracin" and "bacitracin salts" are used interchangeably and refer to all of the various forms of bacitracin, and mixtures thereof, which are complexed with a divalent metal ion. Examples of divalent metal ions which can be complexed with bacitracin to form a bacitracin salt in accordance with the present invention include, without limitation, $Co^{2+}$, $Cd^{2+}$, $Cu^{2+}$, $Mn^{2+}$, $Ni^{2+}$ and $Zn^{2+}$.

Commercial bacitracin is a mixture of several different bacitracins which differ principally from each other in amino acid composition. A typical commercial mixture comprises the following active bacit racin forms (wt. %) : bacitracin A (54. 0), bacitracin B, (14. 0), bacitracin $B_2$ (12.0), bacitracin $B_3$. (11.0), and other bacitracins (9.0). As shown by nuclear magnetic resonance, the predominant form, bacitracin A ($C_{66}H_{103}N_{17}O_{16}S$), complexes with a divalent metal ion ($Zn^{2+}$) by an interaction with four groups in the peptide. These are as follows: (a) the thiazole ring between $Ile_1$, and $Cys_2$; (b) the carboxylic group of $Glu_4$; (c) the imidazole ring of $His_{10}$; and, (d) the amino group of $Ile_1$. Two protons are released during complexation. Accordingly, empirical formula of the divalent metal salts of bacitracin differ from that of bacitracin A. The pKa of the amino acid residues involved in the metal ion binding, as well as the pKa of neighboring residues, is decreased. Generally, the overall effect of the metal ion binding is a molecule which is more neutral.

In the absence of a divalent metal ion, bacitracin A possesses a hydrophobic core of aromatic residues and a sufficiently hydrophilic exterior. This gives bacitracin A an ample solubility in polar solvents. However, upon complexation with a divalent metal iony electrostatic interactions cause the peptide to "coil" around the metal atom. This inverts the distribution of the hydrophilic and hydrophobic residues. Accordingly, the metal complex exhibits low solubility in water and increased affinity for hydrophobic structures such as membranes.

The increased hydrophobic structure of bacitracin salts increases their tendency for entering the cell membrane. Therefore, these salts have an enhanced antimicrobial activity when compared to their uncomplexed counterpart.

Nuclear magnetic resonance studies on bacitracin A revealed that it is conformationally unstable in solution. This molecule possesses a flexible structure composed of a series of different conformations which interconvert very quickly. On the other hand, similar studies on zinc bacitracin revealed that it has a much more stable conformation. Here, there is less conformational flexibility than in bacitracin A. This is due to complexation with the divalent metal ion.

Bacitracin A and its divalent metal salts also differ in their relative chemical stability. For example, uncomplexed bacitracin A is subject to oxidation and conversion to bacitracin F, which has little antimicrobial activity. On the other hand, zinc bacitracin resists oxidation (Froeyshov, "The Bacitracins: Properties, Biosynthesis, and Fermentation, In: Biotechnology of Industrial Antibiotics (Vandamme, E.J., ed.) Marcel Dekker, Inc., New York, N.Y., p. 665-694 (1984)).

Moreover, binding of the N-terminal amino acid residue ($Ile_1$) by zinc also prevents deamination. Nuclear magnetic resonance studies have confirmed $Zn^{2+}$ binding by the bacitracin $Ile_1$ residue.

In summary, these NMR results reveal that bacitracin A and zinc bacitracin are different from one another with respect to structure, conformation and chemistry.

The efficacy of bacitracin as an anti-bacterial agent has been demonstrated. Therefore, until now, it has been generally regarded that bacitracins action on protozoa (e.g., *E. histolytica*) was due to the drug's reduction of intestinal bacteria on which the amoeba feeds. However, through experimentation, we have confirmed the study of Gillin and Diamond, *J. Antimicrobe. Chemother.* 8, 305-16 (1981) that bacitracin is directly active against parasitic protozoans, even in the absence of bacteria. Also through experimentation, we have demonstrated, for the first time, that most divalent metal salts of bacitracin are at least an order of magnitude more active against protozoans than uncomplexed bacitracin.

Zinc bacitracin is the preferred bacitracin salt for treating protozoan infection. Unlike metronidazole, the present drug of choice for treating *E. histolytica* infections, zinc bacitracin is nonmutagenic, as shown by a series of prior studies. Zinc bacitracin was devoid of mutagenic potential in histidine auxotrophs of *Salmonella typhimurium* in the absence and presence of a rat liver activating system. In another study, zinc bacitracin induced no significant increase in the mutation frequency at the TK gene locus in a mouse lymphoma cell mutation system with and without activation. In yet another study, zinc bacitracin did not induce any damage to the chromosomal structure of human peripheral lymphocytes, even at high concentrations producing a marked reduction in cell division. In an in vivo study, subacute oral administration of zinc bacitracin in rats for 5 days at levels of 10, 50, and 250 mg/kg live weight, equivalent to dietary concentrations of 100, 500 and 2,500 mg/kg, produced no significant damage to chromosomal structure in rat bone marrow cells. Finally, zinc bacitracin had no significant effect on semiconservative DNA synthesis, unscheduled DNA synthesis (DNA repair) and sucrose sedimentation of nucleoid ("supercoiled" DNA) harvested from spleen cells of rats fed 8.3 and 41 mg/kg (live weight) zinc bacitracin per day, equivalent to dietary concentrations Of 136 and 833 mg/kg, for 7 days. Only a small reduction in nucleoid sedimentation velocity was observed after 24 hours incubation at the higher level of administration.

Since zinc bacitracin is not absorbed from the gut, its oral toxicity is quite low. It has been shown to be non-toxic in both sub-chronic and chronic oral toxicity studies in rats at feed levels up to 1,000 ppm, which is well above the effective concentration required for treating *E. histolytica* infection. The animals tolerated all doses without apparent ill effect. No detectable levels of zinc bacitracin were found in the livers of any animals tested. Necropsies of animals which died during the test revealed no drug-related effects which could be responsible for the deaths.

The bacitracin salts can be compounded with conventional pharmaceutical carriers according to conventional pharmaceutical formulation techniques. The carrier may take a wide variety of forms. For example, for solid oral dosage forms, the carriers may comprise starches, sugars, diluents, granulating agents, lubricants, binders, disintegrating agents and the like. Moreover, the dosage form may comprise powders, capsules or tablets. Controlled release forms may also be utilized. Because of their ease of administration, tablets and capsules represent the most advantageous oral dosage unit form. If desired, tablets may be sugar-coated or enteric-coated, according to standard techniques.

According to one preferred embodiment, zinc bacitracin is administered as a tablet wherein the principal tabletting agent comprises cellulose, more particularly, microcrystalline cellulose. A preferred tablet form has the following composition:

| | |
|---|---|
| Zinc bacitracin (non-sterile) | c.a. 380 mg (25,000 I.U.) |
| Microcrystalline cellulose | 150-250 mg |
| Polyvinylpyrrolidone, crosslinked | 10-40 mg |
| Magnesium stearate | 5-10 mg |
| Tablet weight | 545-680 mg |

Typically, zinc bacitracin has a zinc content of about 5 wt%. Potency, defined as the antimicrobial activity against a sensitive strain Of *Micrococcus uteus*, typically ranges from between about 65 to about 70 IU/mg.

When practicing the present invention, it is presently preferred to treat infection with *Entamoeba histolytica*, *Giardia lamblia*, and *Cryptosporidia* sp. by oral administration of bacitracin salt, preferably in tablet form. One example of a suitable tablet formulation is set out above.

For the treatment of *Tritrichomonas foetus* infection in accordance with the present invention, it is presently preferred to deliver the bacitracin salt in an emulsion, foam or ointments vehicle. The vehicle should be capable of delivering an effective dosage to the penile crypts of the bull and have sufficient viscosity to adhere to the penile and preputial cavity of the animal. It should be fluid enough to be deliverable at low pressure. An emulsion, an expanding foam and/or an ointment will have the desired properties.

While either oil-in-water or water-in-oil emulsions may be used, the latter are preferred due to their higher viscosity. Oil-in-water emulsions may be prepared from mineral, vegetable or animal oils, stabilized as droplets in the water phase by emulsifiers such as sodium stearate, triethanolamine stearate, and sodium stearylsulphate, in concentrations up to 1%. The emulsifier may also comprise one of the polysorbates, which are polyoxyethylene fatty acid esters. In particular, the emulsifier may advantageously comprise polyoxyethylene (20) sorbitan monooleate more commonly known as polysorbate 80.

Water-in-oil emulsions may be prepared from mineral, vegetable or animal oils, where the water phase is stabilized as droplets in the oil phase by emulsifiers such as lecithin, stearyl alcohols, cholesterol and sorbitan, in concentrations up to 5%. The emulsifier may advantageously also comprise one of the fatty acid partial esters of sorbital anhydrides, such as sorbitan monboleate.

Either aqueous or non-aqueous foams may be used for local delivery of the bacitracin salt. The two foams have somewhat different properties regarding expansion volume, surface adherence and reactivity towards divalent metal salts of bacitracin. Non-aqueous foams are typically prepared from polyalcohols like propylene glycol or glycerol, and stabilized with emulsifiers such as any of the emulsifying waxes available from Croda, Inc. under the trademark Polawax® or any. of the polyoxyethylene ethers of higher aliphatic alcohols available from ICI Americas, Inc. under the trademark Brijo®. Isobutane or other polyalcohol-soluble gases can be used as expellers. Aqueous foams may be prepared from a mixture of polyalcohols (propylene glycol, glycerol, etc.) and water, and stabilized with emulsifiers such as the "Softigen" emulsifiers available from Hals AG, Polawax® and/or "Montawax".

According to yet another embodiment, the delivery vehicle may comprise an ointment, prepared from mixtures of oils and waxes, and quantitatively balanced in order to obtain the desired physical, chemical and mechanical properties.

Delivery of these bacitracin salt formulations for the treatment of *T. foetus* infection may be achieved with a propellant such as compressed air or an inert gas. The compressed air or gas will deliver the formulation through an applicator inserted into the animal's preputial cavity. Alternatively, a syringe could be used.

For most bovine trichomoniasis infections, a delivered volume ranging from between about 50-100 ml should ensure treatment of all surface areas. Preferably, during treatment, the applicator should be rotated while within the preputial cavity.

For treatment of the human parasite *Trichomonas vaginalis*, the bacitracin salt formulation is preferably compounded in the form of a molded pessary.

For treatment of *Cryptosporidia* sp. infection, the presently preferred mode of administration of bacitracin salts is the same as that for *E. histolytica*, that is, as an oral tablet. However, the treatment dosage for Cryptosporidia sp. infections generally should range from between about 0.5 to about 5 grams per day. Moreover, it may be necessary to extend treatment to exceed 20 days.

In the treatment of *Tritrichomonas gallinae* infections in gallinaceous birds (i.e., birds having a crop), it is presently preferred to administer the bacitracin salt in the bird's food. The drug should be administered in such a manner that it would be retained in the crop. A preferred dosage will generally range from between about 100 to about 500 grams of the bacitracin salt per ton of bird feed.

Divalent metal salts of bacitracin may be administered according to the invention in any amount sufficient to achieve alleviation of the particular protozoan infection. Such amounts may vary depending in part upon the extent and stage of the disease and/or infection, the age, sex, size and weight of the patient, and/or whether the treatment is prophylactic or therapeutic in nature. Because of the low toxicity of bacitracin divalent metal salts such as zinc bacitracin when administered orally, their usage for prophylaxis in locations where certain protozoans are present is advisable.

Those skilled in the art should be able to determine the appropriate daily dosage and treatment regimen to suit the specific circumstance. Generally, the daily oral dosage of bacitracin salt for humans will range from between about 0.5 to about 5.0 grams of active agent per day, preferably, from between about 1.0 to about 3.0 grams per day. Generally, treatment will be continued for a time period ranging from between about 3 to about 10 days. Greater or lesser amounts of drug and treatment intervals may be utilized as required. For example, according to the results of a clinical study hereinafter reported, a dosage of about 1.5 grams of zinc bacitracin per day, over the course of from about three to about five days, proved effective in eradicating *E. histolytica* infection in humans at various stages of infection.

In accordance with this invention, the divalent metal salts of bacitracin can be used to efficiently treat humans or animals infected by free-living and/or parasitic protozoan. Examples of such include, without limitation, *Entamoeba, histolytica, Trichomonas vaginalis, Tritrichomonas foetus, Tritrichomonas gallinae, Giardia lamblia, Cryptosporidium parvum, Cryptosporidium sp., and Plasmodium sp.* These and other protozoan organisms are responsible for disease conditions such as amoebic dysentery, bovine-trichomoniasis, babesiosis, theileriosis, toxoplasmosis, leishmaniasis, giardiasis, cryptosporidiosis, and all forms of malaria (human and veterinary), any of which disease conditions may be treated according to the practice of the invention.

The following examples indicate treatment of protozoan-related infections with divalent metal salts of bacitracin, and compare the sensitivity of certain protozoans to bacitracin salts and bacitracin..

It should be noted that the examples are intended to demonstrate select embodiments of the invention and are, in no way, intended to limit the scope thereof.

EXAMPLE I

Entamoeba histolytica Assay

This in vitro study demonstrates that zinc bacitracin is many times more active against *E. histolytica* than bacitracin.

Xenic Culture Study

*E. histolytica* isolates representing three distinct zymodemes (I, II or XIV) were derived from a range of geographical locations. The patients from whom the isolates were obtained were either pathogenic (i.e. presented dysentery), or non-pathogenic (i.e., presented a non-dysenteric stage of infection characterized by passing of cysts or trophozoites). The following table identifies the *E. histolytica* isolates in accordance with the above criteria:

TABLE 1

Identification of *Entamoeba histolytica* Isolates

| Isolate | Origin | Pathogenic/Non-Pathogenic | Zymodeme |
|---|---|---|---|
| T2k | AFRICA | NP[1] | ND[3] |
| T4 | AFRICA | NP | I |
| T6 | AFRICA | NP | I |
| 418 | INDIA | NP | I |
| 70k | NORWAY | NP | I |
| 116k | NORWAY | NP | I |
| AiDO | AFRICA | NP | I |
| 1 | NORWAY | NP | I |
| OMAk | NORWAY | NP | I |
| MS | AFRICA | NP | I |
| BiLO | AFRICA | NP | I |
| GS | AFRICA | NP | I |
| URU1 | AFRICA | NP | I |
| URU19 | AFRICA | NP | I |
| SI | ENGLAND | P[2] | II |
| 1246 | ENGLAND | P | II |
| DA | AFRICA | P | II |
| DOGO | AFRICA | P | II |
| Sh2 | INDIA | P | XIV |
| C1 | INDIA | P | XIV |
| C2 | INDIA | P | XIV |

[1]Isolate from a patient passing cysts or trophozoites, but non dysenteric.
[2]Isolate from a patient presenting with dysentery.
[3]Zymodeme not determined.

Each isolate was a xenic culture, i.e., it contained, in addition to the *E. histolytica* amoeba, the normally occurring patient faecal microflora. The cultures were maintained according to the method of Robinson, *Trans. Roy. Soc. Trop. Med. Hyg.* 62, 285-94, (1968). Bacitracin (70 I.U./mg) and its zinc salt (65 I.U./mg) were obtained from Apothekernes Laboratorium A.S (Oslo, Norway). Following microtitre-assay standardization and pilot testing of the drugs (results not presented), the following assay procedure was established. Bacitracin was screened over the range of 20.0–0.625 mg/ml by doubling dilution. 30 mg/ml bacitracin was also examined. Zinc bacitracin was screened by doubling dilution over the range of 10.0–0.156 mg/ml. The remaining wells were run as controls. An initial stock solution of 75 mg/ml bacitracin was prepared in starch-free Robinson medium (SFRM). Subsequent to loading the first set of wells, the stock was diluted with SFRM to 50 mg/ml, which was used to prepare the remaining concentrations. Zinc bacitracin was dissolved to 250 mg/ml in acidified distilled water (60 μl conc. HC1/ml distilled water) and subsequently added dropwise to 9 ml SFRM (25 mg/ml). 100 μl volumes of both drugs were then double-diluted in SFRM to provide 2.5X concentrates of the required final concentrations in the microtitre plates. 50 μl of a 25 mg% starch (BDH) solution (in SFRM) was then added to each well. 16–18 hours before the end of the required 48-hour culture period, the amoeba isolates were passaged to fresh tubes containing starch-free Robinson medium. At the end of the culture period, the amoebae were harvested in a small volume of medium and resuspended in at least 20 volumes SFRM. The suspensions were centrifuged at 1000 rpm for 5 minutes prior to re-suspension in fresh medium and counted in a modified Neubauer chamber. Amoebae were centrifuged as before and the pellet resuspended to a concentration of $2.5 \times 10^4$/ml SFRM. 100 μl aliquots were then pipetted into respective wells to provide duplicate cultures of each isolate for each concentration assayed. The plates were then placed in an anaerobic chamber (HP11, Oxoid) at 37° C. for 24 hours. While this procedure provided sufficient starch for the amoebae, the concentration was such that at 24 hours the plates were easily read and quantitified by direct observation using an inverted microscope. Viability was assessed by the addition of Trypan blue to a final concentration of 0.1%.

Tables 2 (bacitracin) and 3 (zinc bacitracin) present the results of three studies on 21 xenic cultures of *E. histolytica* isolates. Readings from each of the studies were collected and stored until all three experiments were completed in order to reduce any bias in subsequent readings. Minimun inhibitory and minimum lethal concentrations were given in mg/ml.

TABLE 2

Minimum Inhibitory Concentration (MIC) and Minimum Lethal Concentration (MLC) of Bacitracin in Xenic Cultures of *Entamoeba histolytica*

| Isolate | Experiment 1 | | Experiment 2 | | Experiment 3 | |
|---|---|---|---|---|---|---|
| | MIC | MLC | MIC | MLC | MIC | MLC |
| T2k | 2.5 | 30.0 | 2.5 | 30.0 | 0.63 | 30.0 |
| T4 | 5.0 | 30.0 | 2.5 | 30.0 | 0.63 | 30.0 |
| T6 | 2.5 | 30.0 | 2.5 | 20.0 | 2.5 | 20.0 |
| 418 | 5.0 | 30.0 | 0.63 | 20.0 | 0.63 | 20.0 |
| 70k | 5.0 | 30.0 | 5.0 | 20.0 | 10.0 | 30.0 |
| 116k | 10.0 | 30.0 | 1.25 | 30.0 | 1.25 | 30.0 |
| AiDO | 10.0 | 30.0 | 2.5 | 30.0 | 2.5 | 30.0 |
| 1 | 5.0 | 30.0 | 10.0 | 30.0 | 5.0 | 30.0 |
| OMAk | 2.5 | 30.0 | ND | ND | 1.25 | 30.0 |
| MS | 5.0 | 30.0 | 2.5 | 20.0 | 1.25 | 20.0 |
| BiLO | 5.0 | 30.0 | ND | ND | 1.25 | 20.0 |
| GS | 2.5 | 30.0 | 1.25 | 20.0 | 0.63 | 30.0 |
| URU1 | 2.5 | 30.0 | 2.5 | 20.0 | 1.25 | 30.0 |
| URU19 | 2.5 | 30.0 | ND | ND | ND | ND |
| SI | 2.5 | 30.0 | ND | ND | 2.5 | 20.0 |
| 1246 | 2.5 | 30.0 | 10.0 | 20.0 | 0.63 | 20.0 |
| DA | 2.5 | 30.0 | 5.0 | 30.0 | 0.63 | 20.0 |
| DOGO | 2.5 | 30.0 | 2.5 | 20.0 | 0.63 | 10.0 |
| Sh2 | — | — | 5.0 | 20.0 | 2.5 | 30.0 |
| C1 | 10.0 | 30.0 | 5.0 | 20.0 | 1.25 | 20.0 |
| C2 | 2.5 | 30.0 | 5.0 | 20.0 | 2.5 | 30.0 |

TABLE 3

Minimum Inhibitory Concentration (MIC) and Minimum Lethal Concentration (MLC) of Zinc Bacitracin in Xenic Cultures of *Entamoeba histolytica*

| Isolate | Experiment 1 | | Experiment 2 | | Experiment 3 | |
|---|---|---|---|---|---|---|
| | MIC | MLC | MIC | MLC | MIC | MLC |
| T2k | 0.63 | 5.0 | 0.31 | 5.0 | 0.16 | 2.5 |
| T4 | 0.31 | 2.5 | 0.31 | 2.5 | 0.16 | 2.5 |
| T6 | 0.31 | 2.5 | 0.63 | 2.5 | 0.31 | 2.5 |
| 418 | 0.63 | 5.0 | 0.31 | 2.5 | 0.31 | 2.5 |
| 70k | 0.63 | 2.5 | 0.63 | 2.5 | 0.63 | 2.5 |
| 116k | 0.63 | 2.5 | 0.31 | 1.25 | 0.31 | 2.5 |
| AiDO | 0.63 | 2.5 | 0.16 | 2.5 | 0.16 | 2.5 |
| 1 | 0.63 | 2.5 | 1.25 | 2.5 | 0.31 | 2.5 |
| OMAk | 0.31 | 2.5 | ND | ND | 0.16 | 2.5 |
| MS | 0.63 | 2.5 | 0.63 | 1.25 | 0.63 | 2.5 |
| BiLO | 0.31 | 2.5 | ND | ND | 0.31 | 2.5 |
| GS | 0.63 | 2.5 | 0.63 | 2.5 | 0.31 | 2.5 |
| URU1 | 0.63 | 2.5 | 1.25 | 2.5 | 0.63 | 2.5 |
| URU19 | 0.63 | 2.5 | ND | ND | 0.31 | 2.5 |
| SI | 0.63 | 2.5 | ND | ND | 0.63 | 2.5 |
| 1246 | 0.16 | 2.5 | 0.63 | 2.5 | 0.31 | 1.25 |
| DA | 0.63 | 2.5 | 0.63 | 2.5 | 0.63 | 2.5 |
| DOGO | 0.16 | 2.5 | 0.31 | 2.5 | 0.31 | 1.25 |
| Sh2 | 0.63 | 2.5 | 0.63 | 2.5 | 0.31 | 2.5 |
| C1 | 1.25 | 2.5 | 0.31 | 2.5 | 0.31 | 2.5 |
| C2 | 0.63 | 2.5 | 0.63 | 2.5 | 0.31 | 2.5 |

While the MICs of bacitracin-treated cultures were variable (0.63–10.0 mg/ml) from isolate to isolate and from study to study, the MLCs were readily reproducible (20 or 30 mg/ml). Cultures with MLCc of 30 mg/ml generally presented only a few living parasites at 20 mg/ml. In contrast, zinc bacitracin-treated cultures were more sensitive and reproducible, with MICs of 0.16–1.25 mg/ml and MLCs of 1.25–5.0 mg/ml. However, precipitation occurred at zinc bacitracin concentrations of 5 mg/ml and higher.

Since the data of Tables 2 and 3 were based on doubling dilutions of drug, we examined the sensitivity of *E. histolytica* over a narrower range of drug concentration. The results of a single study are presented in Table 4. Two other isolates were run in the same assay, but were abandoned due to poor controls. Minimum lethal concentrations are given in mg/ml.

TABLE 4

Minimum Lethal Concentrations of Bacitracin and Zinc Bacitracin in Xenic Cultures of *Entamoeba histolytica*

|  | MLC Bacitracin | MLC Zinc Bacitracin |
|---|---|---|
| Isolate 1 | 21 | 1.6 |
| Isolate C1 | 24 | 1.4 |

As can be seen from the data in Table 4, zinc bacitracin was over thirteen times more active than bacitracin in xenic culture.

Example II

Entamoeba histolytica Assay

This study demonstrates that zinc bacitracin kills *E. histolytica* by a direct toxic effect on the amoeba, rather than by merely eliminating the intestinal bacteria upon which the organism feeds.

Axenic Culture Study

Axenic cultures are isolates of amoeba which have been adapted for growth in the absence of bacteria, i.e. they comprise sterile cultures. *E. histolytica* axenic cultures (NIH:200) were maintained according to the method of Diamond, *J. Parasitol.* 54, 1047–56 (1968) in TP-S-1 medium modified by replacing the vitamin solution with 2.5% NCTC 135. Tubes (10 ml, flat-sided) were each primed with $2 \times 10^5$ amoebae and set in an incubator at 37° C. for 1 hour prior to the addition of 1 ml 10X stock drug solution (bacitracin or zinc bacitracin). Amoebae were harvested by cooling tubes at 4° C. for 20 minutes in an ice-bath prior to centrifugation at 1,000 rpm for 8 minutes at 4° C. Assays were performed over 36–48 hours, rather than the 24 hour period used for xenic cultures, due to the more extended division time of axenic cultures. All assays were performed in triplicate.

All amoeba were killed in 48 hours in the presence of 20 mg/ml bacitracin. Cell number reductions of 76.4% and 92.3% compared to controls were observed when tubes were incubated with 2.5 and 5 mg/ml bacitracin, respectively. This reduction increased to 97.7% at 10 mg/ml, and 99.9% at 15 mg/ml bacitracin. In contrast, zinc bacitracin produced a 68.3% reduction at 1 mg/ml, a 90.6% reduction at 2 mg/ml, and over a 99.5% reduction at 5 mg/ml. While these results indicate that 2–3 times the concentration of zinc bacitracin is required for lethality in axenic as opposed to xenic amoeba cultures, a direct toxic effect on *E. histolytica* has been established. The action of the bacitracins on the amoeba is not simply a secondary effect of the elimination of the intestinal flora upon which *E. histolytica* subsists.

EXAMPLE III

Amoebiasis Clinical Study

Human patients were given zinc bacitracin in 25,000 I.U. tablet form in a single daily dose of 100,000 I.U. All patients had clinical disease and laboratory signs of amoebiasis. Cysts and trophozoites of *E. histolytica* were detected initially by wet preparation screening of faeces, and later confirmed by the formal-ether technique. Full parasitological cure was based upon the presentation of 1–2 negative stool samples within one week post treatment.

In a dose-effect segment of the study, two groups of symptomatic *E. histolytica* cyst or trophozoite passers attending an outpatient clinic for abdominal pains were treated for either ten or five days. The results are set forth in Table 5:

TABLE 5

Dose-Effect Study of Symptomatic Cyst & Trophozoite Passers

| Days of Treatment | Number of Patients | Number Responding | Number Relapsing |
|---|---|---|---|
| 10 | 9 | 9 | 0 |
| 5 | 5 | 5 | 0 |

In a dose-duration study, three groups of patients were observed: Group 1 - symptomatic cyst and trophozoite passers; Group 2 - dysenteric patients with bloody diarrheas; and, Group 3 - asymptomatic cyst passers. The results are set forth in Tables 6–8.

TABLE 6

Dose-Duration Study of Symptomatic Cyst and Trophozoite Passers

| Days of Treatment | Number of Patients | Number Responding | Number Relapsing |
|---|---|---|---|
| 5 | 5 | 5 | 1 |
| 3 | 12 | 12 | 2 |
| 2 | 9 | 5 | 3 |
| 1 | 2 | 1 | 1 |

TABLE 7

Dose-Duration Study of Dysentery Cases

| Days of Treatment | Number of Patients | Number Responding | Number Relapsing |
|---|---|---|---|
| 3 | 5 | 5 | 1 |

TABLE 8

Dose-Duration Study of Asymptomatic Cyst Passers

| Days of Treatment | Number of Patients | Number Responding | Number Relapsing |
|---|---|---|---|
| 5 | 9 | 9 | 4 |
| 3 | 9 | 8 | 2 |

In the dose-effect study, 9 patients were treated for 10 days with a cure rate of 100%. Where examined, there were no clinical or parasitological relapses (Table 5). Five patients were treated for 5 days and all cleared their disease.

The dose-duration study of Group I patients (symptomatic cyst and trophozoite passers) included 5 .p cases treated for, 5 days with full effect except for one patient relapse at day 12 following treatment (Table 6). In 12 patients treated for 3 days, the primary cure rate was 100%, but 2 patients relapsed at days 6 and 10 (16%). In 9 patients treated for two days, the cure rate was 55% and the relapse rate 60%. Two patients were treated for I day without success.

In the dose-duration study of Group 2 patients (dysenteric patients with bloody diarrheas), 5 cases responded with full clinical and parasitological cure on a three-day regimen, but one patient had a parasitological relapse on day 12 (Table 7).

bic environment. An Oxoid HP 11 anaerobic gas chamber and BR 38 gas generating kit were used to produce the anaerobic environment. Sequential dilution of bacitracin (i.e., 500-3,500 IU in 500 IU intervals) and zinc bacitracin (i.e., 100-400 IU in 50 IU intervals) was used rather than the doubling dilutions as used with metronidazole. The results are set forth in Table 9.

TABLE 9

Sensitivity of Metronidazole-Sensitive and Metronidazole-Insensitive Isolates of *Trichomonas vaginalis* to Bacitracin and Zinc Bacitracin

| Sensitivity to Metronidazole | Isolate | Bacitracin | | Zinc Bacitracin | | Metronidazole | |
|---|---|---|---|---|---|---|---|
| | | Anaerobic MLC (IU/ml) | Aerobic MLC (IU/ml) | Anaerobic MLC (IU/ml) | Aerobic MLC (IU/ml) | Anaerobic MLC (µg/ml) | Aerobic MLC (µg/ml) |
| Sensitive | 1031 | 2000 | 2000 | 350 | 250 | 4 | 40 |
| | 1043 | 2000 | 2500 | 350 | 350 | <1 | 20 |
| | 1044 | 2000 | 2000 | 300 | 250 | <1 | <10 |
| | 1064 | 1500 | 1500 | 300 | 250 | <1 | — |
| | 1065 | 2000 | 2000 | 400 | 300 | <1 | <10 |
| | 1165 | 2000 | 2000 | 250 | 350 | <1 | 40 |
| | 1910 | 2000 | 2000 | 350 | 400 | 2 | 40 |
| | 6950 | 2000 | 2000 | 400 | 350 | 2 | 20 |
| | UCH-1 | 2000 | 2000 | 400 | 400 | 4 | 40 |
| | UCH-2 | 2500 | 2500 | 400 | 350 | 2 | <10 |
| | UCH-M1 | 2000 | 2000 | 250 | 250 | 4 | 20 |
| | UOB-1 | 2000 | 2000 | 400 | 400 | <1 | 20 |
| Insensitive | 89532.2 | 2000 | 2000 | 350 | 350 | 2 | 200 |
| | 90576 | 2000 | 2500 | 350 | 250 | 2 | 80 |
| | CDC85 | 2000 | 1500 | 350 | 350 | 20 | 200 |
| | IR78 | 2000 | 2000 | 300 | 300 | 4 | 200 |
| | PHLS289 | 2500 | 2000 | 250 | 200 | 8 | 60 |
| | STH-1 | 2000 | 2000 | 350 | 250 | 8 | 60 |

The dose-duration study of Group 3 (asymptomatic cyst passers) included 9 subjects on a fiveday regimen. All 9 cleared between day 2 and 4 (Table 8). After two weeks, 44% showed parasites in their stools again. The three-day regimen included 9 cases. One subject did not respond. Two patients relapsed.

The clinical results indicated that individuals with both asymptomatic amoebiasis and symptomatic disease, as well as patients with signs of mucosal invasive disease with bloody diarrheas, are treatable with zinc bacitracin. No side effects were reported.

These results, indicating 100% cure with 100,000 I.U. daily zinc bacitracin for 3-5 days, may be compared with the earlier study by Most et al., Am. J. Troy, Med. 30, 491-497 (1950), where a 100% cure rate could not be achieved with the same daily bacitracin dosage over ten days.

EXAMPLE IV

Trichomonas vaginalis Assay

This study compares the sensitivity of *T. vaginalis* to bacitracin and zinc bacitracin.

*T. vaginalis* isolates were collected from human subjects of these isolates, 12 were sensitive to metronidazole; and, 6 were insensitive to metronidazole. All isolates were treated with either bacitracin or zinc bacitracin. The treatment was performed in accordance with the method described in Meingassner, J.G. and Thurner, J., "Strains Of Trichomonas Vaginalis Resistant To Metronidazole And Other 5-Imidazoles", *Antimicrobial Agents and Chemotherapy*, 15, pp. 254-257 (1979).

Prior to being diluted with the medium, the bacitracins were initially solubilized in water to 250 mg/ml. The zinc salt was solubilized in acidified water (60 µl HCl/ml). Duplicate plates of each isolate were prepared. one set of plates was exposed to an aerobic environment; and, the second set was exposed to an anaero- As can be seen from Table 9, metronidazolesensitive isolates (i.e., those having a MLC<40 µg/metronidazole under aerobic culture conditions) displayed bacitracin MLCS ranging from 1,500 to 2,500 IU/ml (i.e., 21.44-35.71 mg/mi) and zinc bacitracin MLCs ranging from 200 to 350 IU/ml (i.e., 3.13-5.47 mg/ml). Thus, zinc bacitracin is approximately 4 to 10 times more potent than bacitracin against *T. vaginalis* infection.

The activity of the bacitracins against the axenic *T. vaginalis* cultures indicates that the drugs are directly active against the parasite, as opposed to being active via a secondary route (e.g., privation of nutrition by the effect of the drugs on bacteria). The fact that the bacitracins were effective against both metronidazole-sensitive and metronidazole-insensitive isolates indicates that the bacitracins act by a different mechanism than metronidazole.

EXAMPLE V

Trichomonas vaginalis Assay

This study demonstrates the effectiveness of other bacitracin salts against *T. vaginalis isolates.*

The procedure of Example IV was repeated, substituting bacitracin salts of the following metals for zinc bacitracin: nickel, cadmium, cobalt, manganese, copper and iron. The MLCs of the bacitracin salts were out of range. However, the MICs indicate that, with the exception of ferrous bacitracin, complexation with a divalent metal salt enhanced the activity of bacitracin. The results are set forth in Table 10:

TABLE 10

Minimal Inhibitory Concentrations of Bacitracin and Divalent Metal Salts of Bacitracin Against *Trichomonas vaginalis* Isolates

| | Isolate | |
|---|---|---|
| Drug | UCH1 MIC (mg/ml) | 1910 MIC (mg/ml) |
| Bacitracin | 10.00 | 10.00 |
| Zinc Bacitracin | 2.50 | 2.50–5.00 |
| Nickel Bacitracin | 1.25 | 2.50 |
| Cadmium Bacitracin | 0.31 | 0.15 |
| Cobalt Bacitracin | 1.25 | 1.25 |
| Copper Bacitracin | 2.50 | 1.25 |
| Manganese Bacitracin | 0.15 | 1.26 |
| Ferrous Bacitracin | >10.00 | >10.00 |

EXAMPLE VI

Zinc Bacitracin Molded Pessary

A typical zinc bacitracin pessary for the treatment of *T. vaginalis* has the following composition:

| | | Specification |
|---|---|---|
| Active ingredient | | |
| Zinc bacitracin | 27,500 IU (EP) | Ph. Eur. |
| Excipient | | |
| Hard Fat (Novata BD) | 1,450 mg | Ph. Eur. |
| Pessary weight | 1,830 mg | |

The amounts of zinc bacitracin and fat are adjusted according to the strength of the zinc bacitracin to insure that each molded pessary contains 27,500 IU (EP) (included 10% excess).

EXAMPLE VII

Tritrichomonas foetus Assay

The effectiveness of treating bovine trichomoniasis with bacitracin versus a bacitracin salt is demonstrated. *T. foetus* isolates were collected and treated with bacitracin or zinc bacitracin in accordance with the procedure of Example IV. of the *T. foetus* isolates which were treated, five were isolated from geographically separate outbreaks of bovine trichomoniasis in Northern California (i.e., Isolate Nos: TF.7, TF.3741, S10, 138 and 121). one of the treated *T. foetus* isolates came from the American Type Culture Collection-strain (i.e., Isolate No: ATCC 30166).

Duplicate plates of each isolate were prepared. One set of plates was exposed to an aerobic environment; and, the second set was exposed to an anaerobic environment. An Oxoid HP 11 anaerobic gas chamber and BR 38 gas generating kit were used to produce the anaerobic environment. Sequential dilution of bacitracin (7–49 mg/ml) and zinc bacitracin (1.5–7.5 mg/ml) was employed. The results are set out in Table 11.

TABLE 11

Sensitivity of *Tritrichomonas foetus* Isolates to Bacitracin and Zinc Bacitracin

| | Bacitracin | | Zinc Bacitracin | |
|---|---|---|---|---|
| Isolate | Anaerobic MLC (mg/ml) | Aerobic MLC (mg/ml) | Anaerobic MLC (mg/ml) | Aerobic MLC (mg/ml) |
| ATCC 30166 | 28 | 28 | 6 | 6 |
| TF.7 | 28 | 28 | 6 | 6 |
| FT.3741 | 28 | 28 | 5 | 6 |
| S10 | 28 | 28 | 6 | 6 |
| 138 | 28 | 28 | 6 | 6 |
| 121 | 28 | 28 | 6 | 6 |

The data demonstrates that zinc bacitracin has five times the potency of bacitracin against *T. foetus*. Effectiveness of the bacitracins against axenic *T. foetus* cultures again demonstrates that the drugs are directly active against the parasite, as opposed to being active via a secondary route (e.g. privation of nutrition by the effect of the drugs on bacteria). The fact that the activity of both bacitracin and zinc bacitracin are independent of the culture conditions indicates that these drugs act by different mechanisms from that of metronidazole.

EXAMPLE VIII

Oil-In-Water Zinc Bacitracin Emulsion

A zinc bacitracin oil-in-water emulsion, suitable for treatment of bovine trichomoniasis, may be prepared by combining the following:

| Paraffin oil | 10.0 g |
|---|---|
| Polysorbate 80 (Tween ®80) | 0.5 g |
| Water | 84.5 g |
| Zinc bacitracin | 5.0 g |

Zinc bacitracin is mixed with paraffin and polysorbate 80. The bacitracin/oil mixture is then dispersed into the water phase by an emulsification device.

Example IV

Water-In-Oil Zinc Bacitracin Emulsion

A zinc bacitracin water-in-oil emulsion, suitable for treatment of bovine trichomoniasis, may be prepared by combining the following:

| Paraffin oil | 60.0 g |
|---|---|
| Sorbitan Monooleate (Span ®80) | 2.0 g |
| Water | 28.0 g |
| Zinc bacitracin | 10.0 g |

Zinc bacitracin is mixed with paraffin oil and sorbintan monooleate. Water is then dispersed in the oil phase by use of an emulsification device.

EXAMPLE X

Zinc Bacitracin Non-Aqueous Foam

A zinc bacitracin non-aqueous foam having the following composition may be prepared:

| Emulsifying Wax (Polawax ®) | 0.74 g |
|---|---|
| Polyoxyethylene stearyl ether (Brij ®76) | 2.99 g |
| Propylene glycol | 80.77 g |
| Isobutane | 5.50 g |
| Zinc bacitracin | 10.00 g |

All components, except isobutane and zinc bacitracin, are mixed (i.e., solid compounds are melted and mixed with the fluids). The zinc bacitracin is added after cooling. The mixture is then filled in cans which were sealed. Expeller gas (isobutane) is added at high pressure through the can valve. The contents are then thoroughly mixed. The product may be used in the treatment of bovine trichomoniasis.

EXAMPLE XII

Zinc Bacitracin Acrueous Foam

A zinc bacitracin aqueous foam having the following composition may be prepared:

| | |
|---|---|
| Polawax ® | 1.70 g |
| "Montawax" | 1.80 g |
| "Softigen" | 17.00 g |
| Propylene glycol | 36.00 g |
| Water | 28.00 g |
| Isobutane | 5.50 g |
| Zinc bacitracin | 10.00 g |

All components, except isobutane and zinc bacitracin, are mixed (i.e., solid compounds are melted and mixed with the fluids). The zinc bacitracin is added after cooling. The mixture is then filled in cans which are sealed. Expeller gas (isobutane) is added at high pressure through the can valve. The contents are then thoroughly mixed. The product may be used in the treatment of bovine trichomoniasis.

EXAMPLE XIII

Zinc Bacitracin Ointment

A zinc bacitracin ointment having the following composition is prepared:

| | |
|---|---|
| Vaseline | 75 g |
| Paraffin Oil | 15 g |
| Zinc bacitracin | 10 g |

The vaseline is melted at 70° C. The paraffin oil is added and the zinc bacitracin is thoroughly mixed into the hydrocarbon base. The product is useful for the treatment of bovine trichomoniasis.

EXAMPLE XIV

Tritrichomonas gallinae Assay

This study compares the activity of bacitracin and zinc bacitracin against *Tritrichomonas gallinae*.

A single *T. gallinae* isolate was collected and treated with bacitracin or zinc bacitracin in accordance with the procedure of Example IV.

Duplicate plates of the isolate were prepared. one plate was exposed to an aerobic environment. The second plate was exposed to an anaerobic environment. Sequential dilution of (500–3,500 IU in 500 IU intervals) and zinc bacitracin (100–400 IU in 50 IU intervals) was used rather than the doubling dilutions as used with metronidazole. Zinc bacitracin was initially solubilized to 250 mg/ml in acidified water (60 HC/Ml prior to dilution with the medium. The results are set out in Table 12.

TABLE 12

Sensitivity of *Tritrichomonas gallinae* Isolates to Bacitracin, Zic Bacitracin and Metronidazole

| | Bacitracin | | Zinc Bacitracin | | Metronidazole |
|---|---|---|---|---|---|
| Isolate | Anaerobic MLC (IU/ml) | Aerobic MLC (IU/ml) | Anaerobic MLC (IU/ml) | Aerobic MLC (IU/ml) | Anaerobic MLC (µg/ml) |
| GH85 | 1500 | 2000 | 300 | 250 | 2 |

According to Table 12, the MLC of bacitracin ranged from 1,500–2,000 IU/ml (i.e., 21.43–28.57 mg/ml), depending upon culture conditions. On the other hand, the MLC of zinc bacitracin ranged from 250–300 IU/ml (i.e., 3.91–4.87 mg/ml). Accordingly, zinc bacitracin is approximately 5 to 8 times as potent as bacitracin against *T. gallinae*.

The data also demonstrates that the drugs are directly active against the parasite, as opposed to being active via a secondary route (e.g., privation of nutrition by the effect of the drugs on bacteria).

EXAMPLE XV

Giardia lamblia Assay

This study compares the activity of bacitracin and zinc bacitracin against *Giardia lamblia* isolates.

A Portland isolate of *G. lamblia* was treated with bacitracin and zinc bacitracin according to the procedure of Example IV.

An Oxoid HP 11 anaerobic gas chamber and BR 38 gas generating kit were used to produce an anaerobic environment. Sequential dilution of bacitracin (i.e., 500–3,500 IU in 500 IU intervals) and zinc bacitracin (i.e., 100–400 IU in 50 IU intervals) was used rather than the doubling dilutions as employed with metronidazole. Zinc bacitracin was initially solubilized to 250 mg/ml zinc in acidified water (60 µl HCl-ml) prior to dilution with the medium. The parasites were incubated in the presence of the treating reagent for 2 4 hours. The viability of the parasites was based on morphology and motility. The results are set out in Table 13.

TABLE 13

Sensitivity of *Giardia lamblia* Isolates to, and the Minimum Inhibitory Concentration of Bacitracin, Zinc Bacitracin and Metronidazole

| | Bacitracin | | Zinc Bacitracin | | Metronidazole | |
|---|---|---|---|---|---|---|
| Isolate | MLC (IU/ml) | MLC (IU/ml) | MLC (IU/ml) | MLC (IU/ml) | MLC (µg/ml) | MLC (µg/ml) |
| Portland | 2500 | >3500 | 400 | >400 | <1 | 2 |
| | 2000 | >3500 | 150 | 300 | <1 | <1 |

The MICs of 2.3–6.3 mg/ml for zinc bacitracin versus 28.6–35.7 mg/ml for bacitracin confirms that, under these conditions, zinc bacitracin is approximately 5 times as potent as bacitracin against *G. lamblia*.

EXAMPLE XVI

G. Lamblia Clinical Study

*G. lamblia* infected patients in Sweden and Remania were treated with 200,000 IU zinc bacitracin in the form of tablets each day (i.e., 25,000 units per tablet, 4 tablets twice daily) for a ten day period. Based upon this dosage, 6 of the ten metronida-zole-resistant patients in Sweden responded to this regime. In addition, all of the 11 non-selected patients in Romania responded to this regime. Eight of these 11 non-selected patients remained clear of infection for the length of the study.

EXAMPLE XVII

Cryptosporidium Parvum Patient Study

The patient was a 12 year old boy, weighing approximately 30 kg. For years, the patient had suffered from moderate diarrhea. Prior to being treated with zinc bacitracin, the patient's stool repeatedly tested positive for intestinal Cryptosporidia. The patient was initially treated with 30,000 units of zinc bacitracin thrice daily. stool samples for parasitology testing were obtained at regular intervals during and after treatment. After 8 consecutive days, the zinc bacitracin was discontinued due to an intercurrent influenza-like febrile disease. The patient received sulfonamide and cefalexin for the influenza during the hiatus. The zinc bacitracin treatment resumed approximately one month later and continued for two weeks thereafter.

After the treatment period, it was observed that the drug was well-tolerated by the patient. No stool parasites were detected over the course of the treatment period, clearly demonstrating the effect against the disease. However, one week after the final discontinuation of treatment, the patient began to once again test positive for intestinal cryptosporidia. This indicates that with an optimal dose-regimen of zinc bacitracin the complete eradication of the cryptosporidia is possible with this otherwise incurable disease.

The present invention may be embodied in other specific forms without departing from the spirit or essential attributes thereof. Accordingly, reference should be made to the appended claims, rather than to the foregoing specification, as indicating the scope of the invention.

We claim:

1. A method of treating infection by a protozoan comprising administering an effective amount a divalent metal salt of bacitracin to an animal or human in need of such treatment.

2. A method according to claim 1 wherein the bacitracin salt comprises a salt of at least one bacitracin selected from the group consisting of bacitracin A, bacitracin $B_1$, bacitracin $B_2$, bacitracin $B_3$, bacitracin $C_1$, bacitracin $C_2$. bacitracin $C_3$, and any combination thereof.

3. A method according to claim 1 wherein the bacitracin salt is selected from the group of bacitracin salts consisting of salts of $Co^{2+}$, $Cd^{2+}$, $Cu^{2+}$, $Mn^{2+}$, $Ni^{2+}$, $Zn^{2+}$, and any combination thereof.

4. A method according to claim 3 wherein the bacitracin salt comprises zinc bacitracin.

5. A method according to claim 1 for treatment of *Trichomoas vaginalis* infection.

6. A method according to claim 1 for the treatment of *Tritrichomonas foetus* infection.

7. A method according to claim 1 for the treatment of *Tritrichomonas gallinae* infection.

8. A method according to claim 1 for the treatment of *Cryptosporidium* sp. infection.

9. A method According to claim 1 for the treatment of Gtardia lamblia infection.

10. A method according to claim 1 for treatment of *Entamoeba histolytica infection.*

11. A method according to claim 10 comprising orally administering zinc bacitracin to a human 12. A method according to claim 11 Wherein the daily dosage of zinc bacitracin is from about 0.5 grams to about 5 grams.

13. A method according to claim 12 wherein the daily dosage of zinc bacitracin is from about 1 gram to about 3 grams.

14. A method according to claim 12 wherein the daily dosage is administered for from about three days to about ten days.

15. A method according to claim 13 wherein the daily dosage is administered for from about three days to about ten days.

16. A method according to claim 1 comprising administering a composition comprising a bacitracin divalent metal salt and a pharmaceutically acceptable vehicle.

17. A method According to claim 16 wherein the composition comprises zinc bacitracin, microcrystalline cellulose, polyvinylpyrrolidone and magnesium stearate.

18. A method according to claim 17 wherein the composition comprises:

(a) from about 150 to about 250 mg of microcrystalline cellulose, (b) from about 10 to about 40 mg of polyvinylpyrrolidone, (c) from about 5 to about 10 mg of magnesium stearate, and (d) the balance comprising zinc bacitracin.

* * * * *